United States Patent
Suchánek et al.

(12)

(10) Patent No.: US 11,331,356 B2
(45) Date of Patent: May 17, 2022

(54) PREPARATION WITH THE MYCOPARASITIC MICROORGANISM PYTHIUM OLIGANDRUM FOR THE TREATMENT OF DERMAPHYTOSES AND YEAST INFECTIONS ON THE SKIN AND MUCOUSES, METHOD OF DETERMING THE CELL'S VIABILITY OF THE MICROORGANISM PYTHIUM OLIGANDRUM AND METHOD OF APPLYING THE PREPARATION

(71) Applicant: BIO AGENS RESEARCH AND DEVELOPMENT—BARD, s.r.o., Prague (CZ)

(72) Inventors: Martin Suchánek, Prague (CZ); Radim Klimeš, Prague (CZ)

(73) Assignee: BIO AGENS RESEARCH AND DEVELOPMENT—BARD, S.R.O., Prague (CZ)

( * ) Notice: Subject to any disclaimer, the term of this patent is extended or adjusted under 35 U.S.C. 154(b) by 145 days.

(21) Appl. No.: 16/314,108

(22) PCT Filed: Aug. 22, 2016

(86) PCT No.: PCT/CZ2016/000095
§ 371 (c)(1),
(2) Date: Dec. 28, 2018

(87) PCT Pub. No.: WO2018/001392
PCT Pub. Date: Jan. 4, 2018

(65) Prior Publication Data
US 2020/0085893 A1 Mar. 19, 2020

(30) Foreign Application Priority Data

Jul. 1, 2016 (CZ) .............................. PV 2016-403
Jul. 8, 2016 (CZ) .............................. PV 2016-417

(51) Int. Cl.

| | |
|---|---|
| *A01N 65/03* | (2009.01) |
| *A61K 36/06* | (2006.01) |
| *A61P 17/00* | (2006.01) |
| *A61P 31/10* | (2006.01) |
| *A61K 9/00* | (2006.01) |
| *A61K 9/10* | (2006.01) |
| *C12N 1/14* | (2006.01) |

(52) U.S. Cl.
CPC ............ *A61K 36/06* (2013.01); *A61K 9/0014* (2013.01); *A61K 9/10* (2013.01); *A61P 17/00* (2018.01); *A61P 31/10* (2018.01); *C12N 1/14* (2013.01)

(58) Field of Classification Search
CPC . A61K 36/06; A61K 9/0014; A61P 17/00–18; A61P 31/10
See application file for complete search history.

(56) References Cited

FOREIGN PATENT DOCUMENTS

| CZ | 9883 U | | 4/2000 |
|---|---|---|---|
| CZ | 302297 B6 | | 2/2011 |
| CZ | WO 2011/054322 | * | 5/2011 |
| CZ | 28816 U1 | | 11/2015 |
| WO | 2011054322 A1 | | 5/2011 |
| WO | 2012076563 A1 | | 6/2012 |

OTHER PUBLICATIONS

English Translation of CZ28816, 123 pages, performed on Oct. 2020 (Year: 2020).*
Andrew Joiner "The Cleaning of Teeth" Chapter 4, pp. 371-405, from Handbook for Cleaning/Decontamination of Surfaces 2007 (Year: 2007).*
Kamoun "Plant Pathogens: Oomycetes (water mold)" Encyclopedia of Microbiology (Third Edition) pp. 689-695, 2009 (Year: 2009).*
Ho "The Taxonomy and Biology of Phytophthora and Pythium" J Bacteriol Mycol Open Access 2018, 6(2): 00174 (Year: 2018).*
Berry et al. "Interaction of the Mycoparasite Pythium oligandrum with other Pythium Species" Biocontrol Science and Technology (1993) 3, 247-260 (Year: 1993).*
N. Benhamou et al: "Pythium oligandrum: an example of opportunistic success", Microbiology, vol. 158, No. Pt 11, Sep. 13, 2012 (Sep. 13, 2012), pp. 2679-2694, XP055346605, GB ISSN: 1350-0872, DOI: 10.1099/mic.0.061457-0.
Neil R Horner et al: "The oomyceteexpresses putative effectors during mycoparasitism ofand is amenable to transformation", Fungal Biology, Elsevier, Amsterdam, NL, vol. 116, No. 1, Sep. 20, 2011 Sep. 20, 2011), pp. 24-41, XP028354656, ISSN: 1878-6146, DOI: 10.1016/J.FUNBIO.2011.09.004.
Barros MES, Santos DA, Hamdan JS "In vitro methods for antifungal susceptibility testing of *Trichophyton* spp." (2006) Mycol Res 110, 1355-1360.
Calderona RA, Fonzi WA "Virulence factors of Candida albicans" (2001) Trends Microbiol 9, 327-335.

(Continued)

*Primary Examiner* — Thane Underdahl
(74) *Attorney, Agent, or Firm* — Dykema Gossett PLLC

(57) ABSTRACT

A preparation containing the mycoparasitic microorganism *Pythium oligandrum* for the treatment of dermatophytoses and yeast infections on the skin and mucous membranes obtained from a dry mixture containing 0.1 to 99.9% weight mycoparasitic microorganism *Pythium oligandrum* and 0.1 to 99.9% auxiliary substances, containing at least one component from a group comprising adsorbent, buffer, moisturizer, deodorant and aroma. This preparation contains 1 to 10×106, with preference of 10 to 50, viable cells of the *Pythium oligandrum* microorganism per 1 ml of aqueous suspension at the site of applying the preparation, whereby the viable cells of the *Pythium oligandrum* microorganism comprise dormant oospores, encysted zoospores and viable coenocytic mycelium. Different application methods of using the preparation are claimed. Exemplary embodiments show the viability of cells using genetic tests and practical tests conducted under the supervision of dermatologists, stomatologists and veterinarians.

16 Claims, 2 Drawing Sheets

Specification includes a Sequence Listing.

(56) References Cited

OTHER PUBLICATIONS

Yacoub A, Berger H, Gerbore J et al. "Draft Genome Sequence of Biocontrol Agent Pythium oligandrum Strain Po37, an Oomycota" (2016) Genome Announcements 4, e00215-16.
Martinez DA, Oliver BG, Graser Y et al "Comparative Genome Analysis of Trichophyton rubrum and Related Dermatophytes Reveals Candidate Genes Involved in Infection" (2012) mBio 3, e00259-12.
Saunte DM, Simmel F, Frimodt-Moller N "In Vivo Efficacy and Pharmacokinetics of Voriconazole in an Animal Model of Dermatophytosis" (2007) Antimicrob Agents Chemother 51, 3317-3321.

* cited by examiner

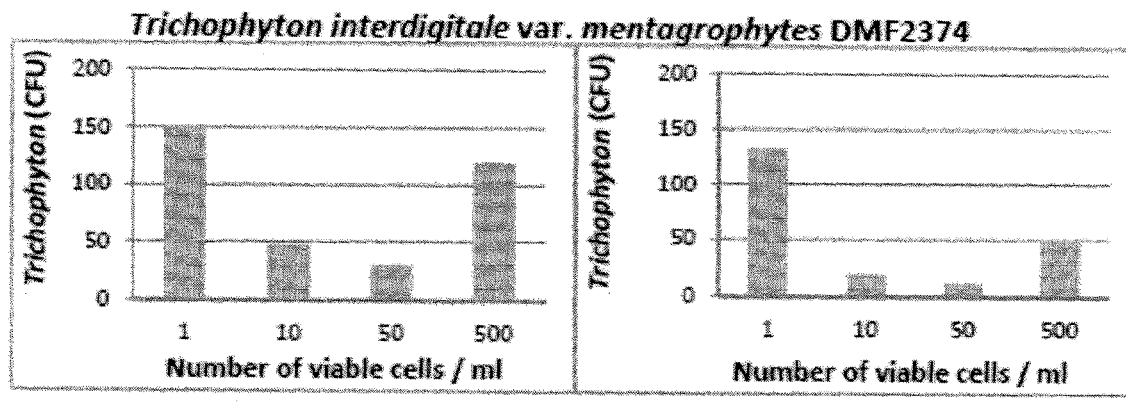
Figure 1A
Figure 1B
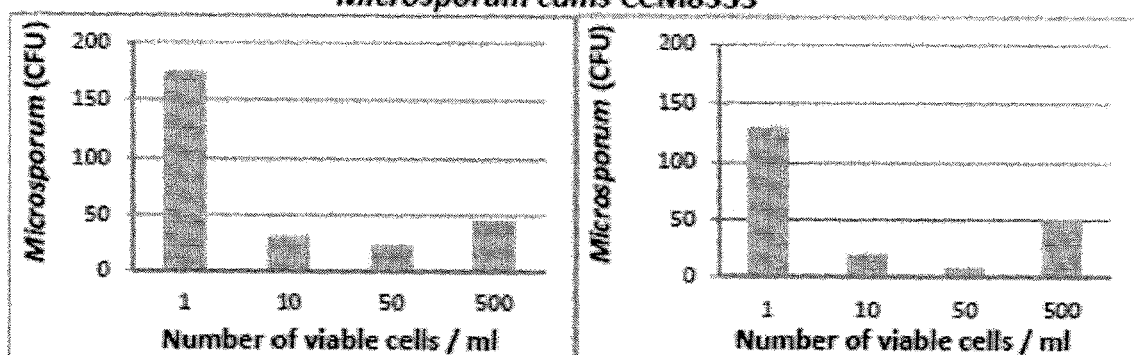
Figure 1C
Figure 1D
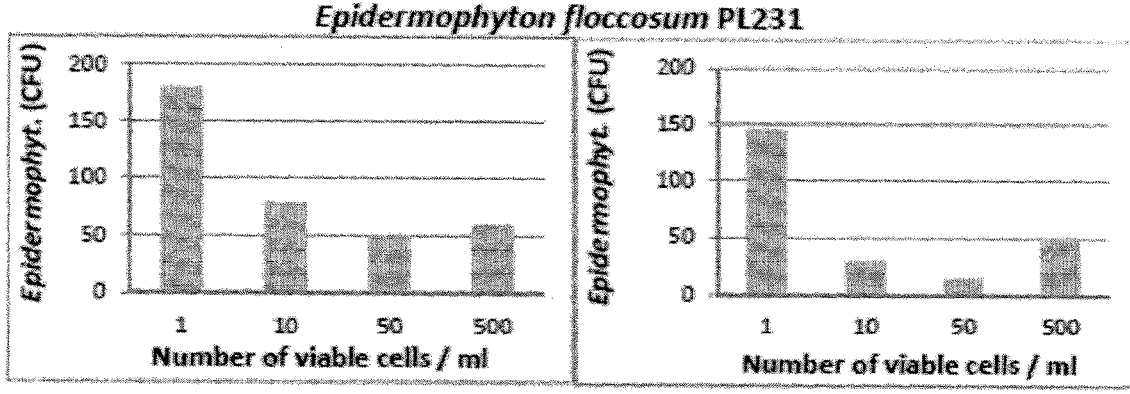
Figure 1E
Figure 1F
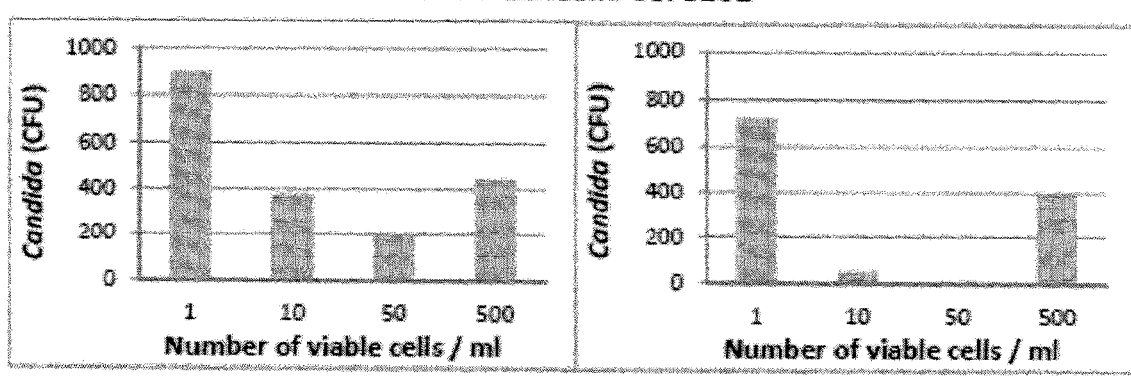
Figure 1G
Figure 1H

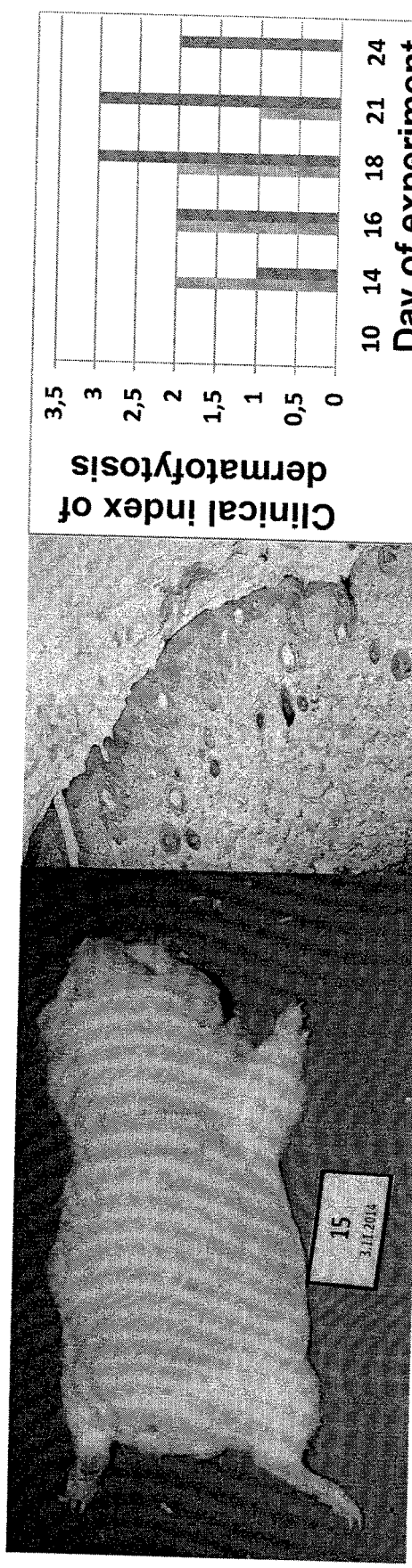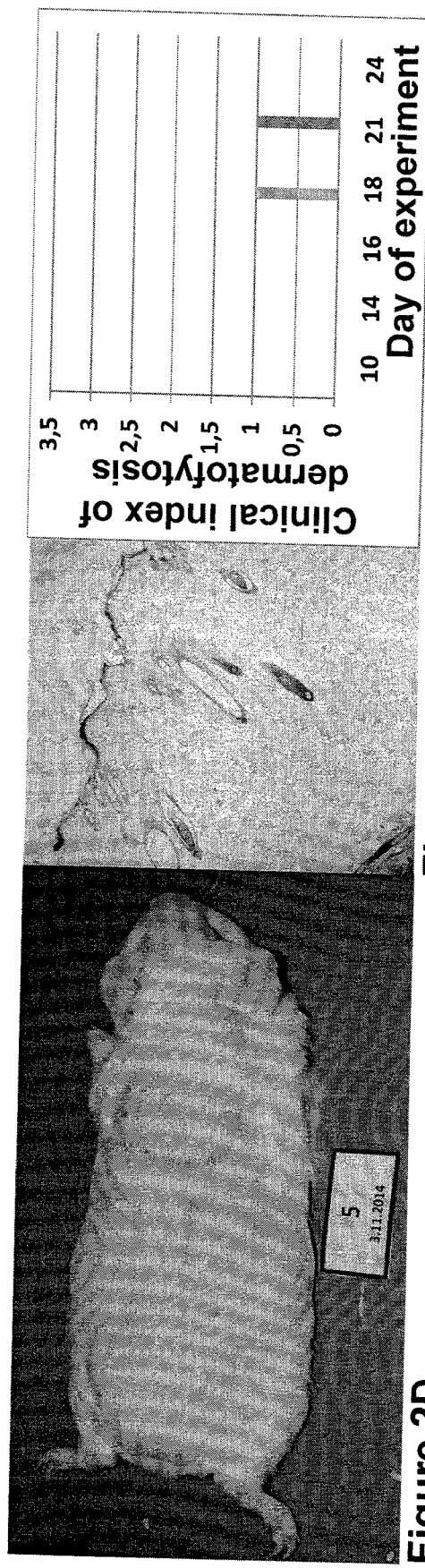

PREPARATION WITH THE MYCOPARASITIC MICROORGANISM PYTHIUM OLIGANDRUM FOR THE TREATMENT OF DERMAPHYTOSES AND YEAST INFECTIONS ON THE SKIN AND MUCOUSES, METHOD OF DETERMING THE CELL'S VIABILITY OF THE MICROORGANISM PYTHIUM OLIGANDRUM AND METHOD OF APPLYING THE PREPARATION

FIELD OF THE INVENTION

The invention concerns a preparation with the mycoparasitic microorganism *Pythium oligandrum* for the treatment of dermaphytoses and yeast infections on the skin and mucous membranes. The preparation comes in the form of an aqueous suspension prepared from a dry mixture containing 0.1 to 99.9% weight mycoparasitic microorganism *Pythium oligandrum* and 0.1 to 99.9% auxiliary substances containing at least one component from the group comprising adsorbent, buffer, moisturizer, deodorant and aroma.

Further, the invention concerns a method of determining the cell's viability of the microorganism *Pythium oligandrum*.

The invention also concerns a method of applying this preparation.

BACKGROUND OF THE INVENTION

Dermaphytoses are fungal infections caused by dermatophytes, keratinophilic fungi that attack, in particular, the skin, the nails and the hair, and that are characterized by a long incubation period. This is mainly facilitated by the minimum reaction by the immune system of the host as a result of effective masking of the surfaces of these keratinophilic fungi from recognition by immunity molecules. Keratinophilic fungi use the keratin protein that occurs in the skin all over the surface of the human body as their vital sustenance by virtue of effective enzymatic degradation and metabolism the digested components. These molds are represented by the species *Trichophyton, Epidermophyton* and *Microsporum*, and the molecular nature of the factors that enable these microorganisms to live their lifestyle has already been identified (6). Skin and mucous membrane mycoses are characterized by different manifestations, usually including irritation, reddening, peeling flakes or even larger areas of skin, the skin sometimes white and macerates in areas of higher sensitivity. Common accompanying symptoms include increased perspiration and socially troublesome odor (smell) symptoms that testify to advanced dysbiosis at the affected sites.

A synonym for dermaphytosis is tinea, wherein, depending on their anatomical localization, the most common forms of dermatophytosis is tinea pedis (on the feet), tinea unguium (under the nails), tinea corporis (fungal infection on the body, mainly the hairless part of the trunk and the proximal part of the lower limbs), tinea cruris (the inguinal area, most commonly in young men during the summer after sweating in tight clothing), tinea capitis (round nidus of short broken hair in the thatch, mostly among children coming into contact with a zoophilic dermatophyte such as *Microsporum canis*). Although dermaphytoses are not usually fatal diseases, they are extremely widespread infections that affect a significant percentage of the population and the symptoms of which make working and social life unpleasant for those that suffer from them.

Opportunistic microbial yeast infections are relatively widespread contemporary ailments among humans, in which the normally harmless commensal yeasts that live in the skin and mucous membranes of a human are activated as a result of the weakening of the immune system during stress, work overload, viral infections or other stressful situations, and transform to the aggressive form characterized by different morphology and metabolism. Research predominantly concentrates on the most common pathogenic yeast *Candida albicans* and its relatives. Molecular and genetic research has recently contributed to identifying the individual factors responsible for this unusual behavior by pathogenic yeasts, which are subsequently important objectives for newly-developed therapies (2).

The therapies currently available for the treatment of dermatophytic and yeast infections are dominated by chemical anti-fungal products from the group of azoles, allylamines and echinocandins, which are, however, notorious for their low effectiveness and frequent side effects that disadvantage a broad group of users (older people, people with diabetes or liver diseases, persons having weakened immunity). Therapies that use these products are relatively very expensive and only have a temporary effect. They are not able to deal in any way with dysbiosis (disruption of the normal, physiological microflora) associated with this type of illness. For this reason, modern treatment to stabilize normal microflora that is effective over the long-term is a major challenge. The use of natural biological products to treat dermaphytoses and yeast infections has thus far only been developed to a minimal extent. The issue of using the *Pythium oligandrum* microorganism to protect the skin is dealt with in utility model CZ 9883U by the employees at Biopreparáty spol. s r. o., inventors Veselý et al, with priority date 18 Nov. 1999. The authors use a suspension of oospores in a quantity which does not exceed $2 \times 10^5$ per 1 g of product to deal with certain skin problems among 9 groups of patients. However, here it is not a case, as the authors of CZ 9883U mistakenly suppose, of eliminating the originators of dermatophytoses where there is no evidence in the document to substantiate such a contention. The authors present laboratory results of the effect of the *Pythium oligandrum* microorganism on the *Scopulariopsis breviacaulis*; however, this microorganism is a saprophytic soil microorganism (and not a dermatophyte). No microbiological examinations were conducted in any of the patients monitored in CZ UV9883 and therefore it is impossible to prove how they are actually affected by dermatophytes. As far as the declared curative effects are concerned, there is no mention in the document that the patients were medically monitored and, in a number of cases, it is more a matter of their subjective feelings to concern the described effects (change in the color of nails, pain disappearing). Patent CZ 302297, owned by the applicant of this invention, used a higher concentration of oospores for the first time following demanding toxicological tests (more than $2 \times 10^5$ per 1 g of product), but does not deal with the issue of dermatophytoses or yeast infections in humans in more detail. On the contrary, the advantage of this solution is that it first clarified the ability of the mycoparasitic microorganism *Pythium oligandrum* to act in an environment other than that of an aqueous suspension, such as in ointments, oils and other forms of application. Moreover, the significance of forms of viable cells of the *Pythium oligandrum* microorganism other than dormant oospores was stressed for the first time, in particular encysted zoospores and viable fragments of mycelium as forms of the *Pythium oligandrum* microorganism most effective in direct mycoparasitism. Utility model CZ 28816 U, owned by the applicants of this invention, deals, in detail, with the issue of opportunistic microbial infections using dual microbial preparations; these, however, are characterized in the classic way using colony-forming units (CFU), the use of which is not without its pitfalls in the case of the *Pythium oligandrum* microorganism.

The disadvantage of the existing solutions and a significant restriction on the road to developing a medicinal product is, therefore, a lack of full understanding of the nature of the effective substance *Pythium oligandrum*, the quantity of which in preparations cannot usually be precisely determined. Consequently, defining the strength and effectiveness of such preparations might be hard to ascertain and reproduce.

THE SUMMARY OF THE INVENTION

The disadvantages specified above are eliminated or significantly restricted by a preparation containing the mycoparasitic organism *Pythium oligandrum* in the treatment of dermatophytoses and yeast infections on the skin and mucous membranes according to claim 1 of this invention, the essence of which is based on the fact that the preparation contains 1 to $10 \times 10^6$, with preference of 10 to 50, viable cells of the microorganism *Pythium oligandrum* per 1 ml of applied aqueous suspension at the site of application, whereby the viable cells of the *Pythium oligandrum* microorganism contain dormant oospores, encysted zoospores and viable coenocytic mycelium.

Further, new subject of the said invention is also method of determining the cell's viability of the microorganism *Pythium oligandrum*. The viability of the cells of the mycoparasitic microorganism *Pythium oligandrum* in the invention submitted is meant as the viability determined by genetic test of the preparation by measuring the level of expression of the constitutive gene for the β-tubulin of the *Pythium oligandrum* microorganism (11), maintained in a medium which is rich in nutrients, in a normal atmosphere at 30° C.

The submitted invention also deals with the method of applying the preparation according to this invention, the essence of which is based on the fact that it includes the following steps: a) the preparation of an aqueous suspension using mechanical dispersion of a dry mixture in the defined volume of lukewarm water or physiological solution to achieve a content of 1 to $10\times10^6$ viable cells, with advantage of 1 to 500 viable cells, and with preference of 10 to 50 viable cells, of the mycoparasitic microorganism *Pythium oligandrum* per 1 ml of aqueous suspension at the site of application; b) the application of the aqueous suspension created in this way depending on the type of diagnosis being treated with the use of the recommended quantity of viable cells of the mycoparasitic microorganism *Pythium oligandrum*; c) the colonization of the viable cells of the mycoparasitic microorganism *Pythium oligandrum* at the place of application according to the diagnosis being treated; d) the reproduction of viable cells of the mycoparasitic microorganism *Pythium oligandrum* at the place of application according to the diagnosis being treated to eliminate dermatophytes or yeasts; and e) the subsequent sporulation and parallel elimination of the preparation in the place of application, facilitating the stabilization and development of the normal microflora to ensuring a long-term curative effect.

The application of the preparation according to the invention in ointments, oils, gels, sprays, moisturizing plasters or powders is carried out in the way known to the experts in the field, with the aim of colonizing the affected place of application with a quantity of viable cells corresponding to the requirements of the particular diagnoses. The physiological solution known to an expert in the field is understood to be, for example, the most common solution of NaCl at a concentration of 9 g per 1 liter, or a physiological solution buffered, for example, by sodium phosphate in a quantity of 10 mg per 1 liter—so-called PBS (phosphate buffered saline).

In principle, any viable cells are able to ensure the colonization and reproduction of the mycoparasitic microorganism *Pythium oligandrum* at the place of application. Dormant oospores that are able to provide viable cells according to local conditions in 24-48 hours after the wetting of the dry mixture are represented in the highest quantity in the preparations according to this invention. The preparations according to this invention also contain encysted zoospores and viable coenocytic mycelium, which are usually able to provide viable cells within 20 minutes of the wetting of the dry mixture.

Colonization of the viable cells of the mycoparasitic microorganism *Pythium oligandrum* at the place of application according to the diagnosis being treated proceeds in the manner known to an expert in the field. In our experience, all these processes in the preparations according to the invention submitted are dependent on the presence of targeted microorganisms such as dermatophytes or yeasts at the place of application. If such target microorganisms for the mycoparasitic microorganism *Pythium oligandrum* are present, this leads to the colonization of viable cells within one to two hours after their attachment to these targeted microorganisms, i.e. dermatophytes or yeasts. The *Pythium oligandrum* microorganism is multiplied within one to two days with the use of nutrients provided by the targeted microorganisms. Viable cells disappear from the place of application within around two weeks of the elimination of the targeted microorganisms. At such time, as the nutrients coming from the targeted microorganisms have been exhausted, we see the transition of the *Pythium oligandrum* microorganism to idle form, meaning sporulation, at the place of application. The dormant oospores created in this way do not survive for long on the skin and mucous membranes as they are regularly removed by dynamic processes in these places of application, i.e. for example, by the separation of dead cells from the affected place and the release of secretions on the mucous membranes. It was empirically ascertained that the mycoparasitic microorganism *Pythium oligandrum* leaving the place of application creates the conditions for the development and stabilization of normal microflora.

When applying the preparation according to the invention with the recommended quantity of viable cells of the mycoparasitic microorganism *Pythium oligandrum*, the applicant empirically ascertained that in treating dermatophytoses and tinea unguium the recommended quantity of viable cells in 1 ml of aqueous suspension is 50, whereas it is 30 in the elimination of yeasts in non-healing wounds and 10 in eliminating yeasts in the oral cavity.

To treat dermatophytoses in the form of tinea unguium according to this invention, a preparation is applied which ideally contains 50 viable cells per 1 ml of preparation in an aqueous suspension, applied in a quantity of 0.15 ml of this suspension per 1 $cm^2$ of the affected area in the form of a wet wrap or in the form of creams, ointments, wet wipes, antimicrobial sprays, moistened patches and powders.

To treat yeast infections in non-healing wounds according to this invention, the preparation is applied in the form of wet healing products using wet compresses ideally containing 30 viable cells per 1 ml of aqueous suspension in a physiological solution and subsequent replacement of wet compresses ideally containing 30 viable cells per 1 ml of aqueous suspension in a physiological solution after 8 hours for a period of 4 days. The wet healing form may also be applied in this concentration in the form of creams, ointments, wet wipes, antimicrobial sprays, moistened patches and the subsequent application of these wet healing products after 8 hours for a period of 4 days.

To treat yeast infections in the oral cavity according to this invention, the application is done by rinsing with the product in an aqueous suspension ideally containing 10 viable cells per 1 ml of application aqueous suspension, in that the rinses are done at least twice a day for a period of 5 consecutive days. Viable cells of the *Pythium oligandrum* microorganism may also be used in toothpastes, gels or oral sprays or the aqueous suspension may be applied to the place being treated using a syringe and needle. All these applications are made at least twice a day for a period of 5 consecutive days.

The main advantage of this invention is the verified viability of the cells of the mycoparasitic microorganism *Pythium oligandrum*, the achievement of a significant and long-term therapeutic effect in the monitored diagnoses, the stability of the preparation, which can be controlled and stored for a longer period, up to 2 years, in dry state and the possibility of more precise and controlled dosage during application. The proven ability of the mycoparasitic microorganism *Pythium oligandrum* to suppress and kill the pathogenic yeast *Candida albicans* could act as a starting point for the development of other preparations to act against other diagnoses, for example vaginal mycoses (candidiases).

Another merit of the invention is, with regard to the current level of technology and the fungicidal biological preparations applied until now, that the preparation according to this invention for the treatment of dermatophytoses and yeast infections on the skin and mucous membranes contains a precisely defined quantity of effective biological substance based on the measurement of the quantity of viable cells of the mycoparasitic microorganism *Pythium oligandrum*, for which a precise molecular method was used to determine viable cells, and the methods of applying the preparation, which were clinically checked.

The invention facilitates the creation of a new generation of preparations that use the *Pythium oligandrum* microorganism with known viability of dormant oospores, encysted zoospores and viable coenocytic mycelium at a low value of microbial contamination. The claimed preparation can be included in the formulations of approved and notified preparations with the new and reproducible curative effects described in the laboratory and practical tests described in the Examples. Suppression of the growth of dermatophytes and pathogenic yeasts in a laboratory suspension test is described, as are the effects during application on dermatophytoses in animals, the treatment of tinea unguium in humans and suppression of pathogenic yeasts in non-healing wounds in diabetic and non-diabetic patients and in the oral cavity.

Several solutions and methodologies were adopted in previous research to determine the viability parameter, although none of these is particularly appropriate for this purpose. These include methods based on different dyeing viable techniques that work well for other types of cells, but known in the *Pythium oligandrum* microorganism for their complicated procedures and none-too-reliable results. The applicant of this invention is aware of the technique of plasmolysis at high concentrations of osmolytes, which provides reliable results, but which is dependent on subjective evaluation by the observer under a microscope. In addition to this, it provides information on the intactness of the *Pythium oligandrum* oospore and not on its viability.

Another group of widely-used methodologies is based on plating of a preparation containing the viable cells of *Pythium oligandrum* on a Petri dish, and subsequently monitoring the number of colonies formed. Unfortunately, the biological nature of *Pythium oligandrum* with its active lifestyle and high speed of linear spread through the coenocytic mycelium is not particularly compatible with these methods, which are otherwise a common standard in microbiology. Often the final possibility for determining viability in preparations of dormant oospores of the *Pythium oligandrum* microorganism is the direct microscopic monitoring of germinating oospores. However, this is, on the contrary, demanding on time and from the perspective of the experimental technique used (video footage).

In light of the problems specified above, great hopes for determining the viability of cells of the *Pythium oligandrum* microorganism were placed on molecular genetic techniques. In our previous work, we attempted to determine viability using a molecular test which was based on qPCR amplification of two independent target gene sequences for this microorganism (4). Nonetheless, this approach did not prove suitable for a number of preparations containing a high content of perished cells of the *Pythium oligandrum* microorganism as a result of the sizeable background of the method. Monitoring certain transcripts constitutively expressed only through living cells of the *Pythium oligandrum* microorganism proved a better solution in this regard, with the transcript for β-tubulin, an abundantly expressed protein of this microorganism, eventually being chosen. The whole experiment takes a week, and includes the cultivation of dormant oospores in a media containing penicillin (to suppress the growth of contaminating bacteria) for a period of 4 days, with samples taken every 24 hours and analyzed using the RT-PCR method for transcription by way of reverse transcriptase. We find the viability value by extrapolating the linearized, measured, exponential curve of the time dependence of growth to zero point.

The advantage of this method of determination is the precise determination of the quantity of viable cells in any preparation of *Pythium oligandrum* microorganism independent of its age and method of preparation. It must be stressed that the viability of cells in preparations containing *Pythium oligandrum* microorganism depends greatly on the method of its preparation and storage. For this reason it is almost impossible to judge for this parameter from the total number of dormant oospores determined in the preparation microscopically (different determinations state the quantity of viable cells of the *Pythium oligandrum* microorganism as 0.01% to 30% of the monitored quantity of dormant oospores, which provides highly uncertain data). It is clear from the reasons specified above that the existing practice of expressing the biological potency (effective doses) of the *Pythium oligandrum* microorganism based on the declared total number of oospores without determining their viability provides poorly reproducible results which are essentially difficult to use, and from which it is not possible to determine the optimum application dosage even following correction for the quantity of the applied substance. When using the newly-established method, the results of laboratory and practical tests were consistent and all pointed to optimum activity in different practical applications in suspensions containing from 10 to 50 viable oospores per ml of application mixture.

Apart from the optimum setting of the application protocol, the measurements of the viability of dormant oospores conducted by the applicant, and described hereunder in the submitted invention are also important for stability tests in monitoring individual batches of preparations. Our practical experiences of effectiveness tests unambiguously prove that when there is a fall in the number of dormant oospores below 330 per g of preparation (10 per ml of applied mixture), there is a decline in effectiveness in eliminating dermatophytes and yeasts, whereas a decline in this value below 33 per g (1 per ml of applied mixture) makes it impossible to guarantee a positive effect. On the contrary, the relationship of concentration and effectiveness in preparations with a very high content of dormant oospores cannot be unambiguously expressed, depending mainly on the purity of such a preparation in relation to the purity of the input ingredients and the meticulousness of the observed technology. When contaminating substances appear, a certain decline in effectiveness can be observed in preparations containing more than 33,000 dormant oospores per 1 g of mixture (1,000 per ml of applied mixture), probably based on the interfering influence of unknown impurities. Such a decline in effectiveness was not observed in highly purified forms of the mycoparasitic oomycete *Pythium oligandrum*, although experience with this type of preparation is currently very limited. Another disadvantage for quick tests of the effectiveness of the *Pythium oligandrum* microorganism, in particular suspension tests conducted with the microconidia of dermatophytes or suspensions of yeasts, is the slow viability of dormant oospores, taking at least 48 hours. For this reason, it would appear to be preferable to replace dormant oospores with encysted zoospores prepared according to the published methods in order to conduct such tests. We ascertained in a direct comparison by way of experiment that both preparations, i.e. the freshly prepared encysted zoospores and the dormant oospores with determined viability, exhibit identical abilities to suppress dermatophytes and pathogenic yeasts. Moreover, in the case of encysted zoospores, it is a storable form of viable cells of the mycoparasitic microorganism *Pythium oligandrum*.

The proposed methods are highly compatible with the requirements placed on testing living microbial medical preparations, in which evidence for colonization and a description of biological, metabolic, morphological and other activities in the place of targeted application are required. The method according to this invention has already been successfully applied in this regard in the treatment of dermatophytoses on animals, where it made it possible to, inter alia, clarify the role of the *Pythium oligandrum* microorganism in the elimination of dysbiosis and the establishment of normal, physiological microbial equilibrium on the skin and in other places of application, for example the mucous membranes (4, 9).

BRIEF DESCRIPTION OF THE DRAWINGS

The technical solution is further described in detail in exemplary embodiments and explained in more detail in the appended schematic drawings, in which FIG. 1 shows a laboratory test of the effectiveness of suppressing dermatophytes and yeasts depending on the quantity of added viable encysted zoospores of the *Pythium oligandrum* microorganism, whereby it refers in more detail to FIG. 1A and FIG. 1B, depicting an effectiveness test with the use of the dermatophyte *Trichophyton interdigitale* var. *mentagrophytes* of the collection strain DMF2374 after 24 and 48 hours of incubation, FIG. 1C and FIG. 1D, depicting an effectiveness test with the use of the dermatophyte *Microsporum canis* of the collection strain CCM8353 after 24 and 48 hours of incubation, FIG. 1E and FIG. 1F, depicting an effectiveness test with the use of the dermatophyte *Epidermophyton floccosum* of the collection strain PL231 after 24 and 48 hours of incubation, FIG. 1G and FIG. 1H, depicting an effectiveness test with the use of the pathogenic yeast *Candida albicans* of the collection strain CCF8261 after 24 and 48 hours of incubation, FIG. 2 shows the clinical results in the treatment of experimental dermatophytosis of guinea pigs, in that the upper part of the figure shows the results for guinea pigs treated with a placebo and the lower part of the figure shows the results for guinea pigs treated with the use of a suspension according to exemplary embodiment 1 of this invention, and in more detail in FIG. 2A, showing photographs of the back of a guinea pig under anesthetic with the application of a placebo on the $16^{th}$ day of treatment with characteristic rediness of the skin in the infected places, FIG. 2B, depicting a histological section of the skin of an animal with the application of a placebo, showing the characteristic proliferation of keratinocytes in the upper layer of the skin in reaction to irritation by untreated dermatophyte, FIG. 2C, depicting the clinical index of dermatophytosis of animals with the application of a placebo on the individual days of treatment, marked as the rediness index (the light gray column) and the skin damage index (the dark gray column), FIG. 2D, showing a photograph of the back of a guinea pig under anesthetic with the application of a suspension according to exemplary embodiment 1 of this invention on the $16^{th}$ day of treatment with a lower level of rediness of the skin in the infected areas, FIG. 2E, depicting a histological section of the skin of an animal with the application of a suspension according to exemplary embodiment 1 of this invention, showing a significantly lower level of proliferation of keratinocytes in a successfully treated animal, FIG. 2F, depicting the clinical index of dermatophytosis of animals with the application of a suspension according to exemplary embodiment 1 of this invention on the individual days of treatment, marked as the redness index (the light gray column) and the skin damage index (the dark gray column).

EXEMPLARY EMBODIMENTS OF THE INVENTION

The solution which we propose is made possible based on further laboratory analyses and practical tests of preparations for human and veterinary medicine according to this invention, build on CZ 302297, the detailed formulation of which was now specified with regard to use in the treatment of dermatophytoses and tinea unguium, the elimination of yeasts from non-healing wounds, and from oral cavity. The invention submitted is further described in detail in the following exemplary embodiments, but should not be limited to them. These exemplary embodiments are presented to ensure that the description is thorough and describes the essence of the invention to the extent of the patented claims.

Example 1

The preparation of dry mixtures containing the *Pythium oligandrum* microorganism of a known viability determined for the treatment of dermatophytoses in guinea pigs, tinea unguium and the elimination of yeasts in non-healing wounds and in the oral cavity.

(Table 1, Table 2, Table 3)

a) Preparation of the Mycoparasitic Microorganism *Pythium oligandrum*

*Pythium oligandrum* strain M1 (strain DV74, sequential protocol of which is found on the next page) was maintained in agar and the starting culture was prepared by a liquid cultivation. Sterilized millet grains (*Panicum miliaceum* L.) were inoculated with the liquid culture. Cultivation proceeded under sterile conditions for a period of around 7 days and the wet biomass was subsequently carefully dried and ground into powder containing particles of an average size of 35 to 50 µm. The quantity of oospores was estimated under the microscope, and the preparation was standardized according to the conditions of CZ 302297 to a content of $7\pm1\times10^6$ oospores per 1 g.

b) Measuring the Viability of Cells of the Microorganism *Pythium oligandrum* in 3 Batches To determine the number of viable cells of the microorganism *Pythium oligandrum*, the applicant of the submitted invention developed an original procedure which is conducted using a genetic test of the preparation in the form of an aqueous suspension according to this invention, measuring the level of expression of the constitutive gene for the β-tubulin of the microorganism *Pythium oligandrum* maintained in a medium rich in nutrients in a standard atmosphere at 30° C.

The quantity of viable cells in the analyzed material was determined using the following procedure: 1 g of dried substance was weighed out and mixed in 100 ml of water in a kitchen blender. 0.5 ml of this suspension was mixed with 4.5 ml of cultivation medium in a six-well culture dish incubated at 30° C., in that 50 µl samples were taken 48 hours, 72 hours and 96 hours after the beginning of incubation. Nucleic acids were extracted and the extract diluted 50× in nuclease-free water. This was followed by reverse transcription and PCR amplification according to the standard protocol in a reaction mixture containing 4 µl of the extract, 1 µl of a mixture of primers for the amplification of the β-tubulin of *Pythium oligandrum* (3) and 5 µl of enzyme mixture. The exponential curve obtained was linearized and extrapolated to the initial zero time. The viability ascertained in this way was 41,700 per g of substance in the case of batch of mycoparasitic microorganism *Pythium oligandrum* (A), 12,500 per g of substance in the case of batch of mycoparasitic microorganism *Pythium oligandrum* (B) and 8,300 per g of substance in the case of batch of mycoparasitic microorganism *Pythium oligandrum* (C). Note: The letters A, B and C in parentheses in this and other embodiments mark the individual batches of the mycoparasitic microorganism *Pythium oligandrum* having the above described viabilities.

The Sequential Protocol of the Applied *Pythium oligandrum* M1 is Shown Below: *Pythium oligandrum* M1_ITS4_RNA of Tested Strain DV74

```
ATCATTACCACACCTAAAAACTTTCCACGTGAACCGTTATAACTATGTTC
TGTGCTTCGTCGCAAGACTTGAGGCTGAACGAAGGTGAGTCTGCGTCTAT
TTTGGATGCGGATTTGCTGATGTTATTTTAAACACCTATTACTTAATACT
GAACTATACTCCGAATACGAAAGTTTTTGGTTTTAACAATTAACAACTTT
CAGCAGTGGATGTCTAGGCTCGCACATCGATAAGAACGCTGCGAACTGCG
ATACGTAATGCGAATTGCAGAATTCAGTGAGTCATCGAAATTTTGAACGC
ATATTGCACTTTCGGGTTATGCCTGGAAGTATGCCTGTATCAGTGTCCGT
ACATCAAACTTGCCTTTCTTTTTTGTGTAGTCAAAATTAGAGATGGCAG
AATGTGAGGTGTCTCGCGCTGTCTTTTTAAAGATGGTTCGAGTCCCTTTA
AATGTACGTTGATTCTTTCTTGTGTCTGCGAATTGCGATGCTATGCTCTT
TGTGATCGGTTTAGATTGCTTTGCGCTGGTGGGCGACTTCGGTTAGGACA
TATGGAAGCAACCTCAATTGGCGGTATGTTCGGCTTTGCCTGACGTTAAG
CTAAGCGAGTGTAGTTTTCTGTGTTTTCCTTGAGGTGTACCTGTCGTGTG
TGAGGTTGATTTAGGCTATATGGTTGCTTGGTTGTGTGGTTTAGCGTTTT
CAGACGCCTGCTTCGGTAGGTAAAGGAGACAACACCAATTTGGGACTGAG
AGTTTACT
```

*Pythium oligandrum* M1, *COXII* Mitochondrial Cytochrome Oxidase of Tested Strain DV74

```
  1  atggaaggta ttattaactt tcatcatgat ttagtatttt ttttaattat tgtgactgtt
 61  tttgtttgtt ggttattatt tagagtaatc gtattattcg atgaaaaaaa aaacccaata
121  cctgctacat ttgtacatgg agcaactatt gaaattattt ggacaacaat tccagcatta
181  attttattaa ccgtagcagt tccatctttt gctttattat attcaatgga tgaaattatt
241  gatccaatta taactttaaa agtaataggt agtcaatggt actggagtta tgaatattct
301  gataatttag aatttgcaga tgaacctta attttgata gttacatggt tcaagataat
361  gacttagaaa taggacaatt taggttatta gaagtagaca accgtgttgt tgtaccaact
421  aatagccata ttagagtttt aataacagct tctgacgttt tacattcatg ggctataccc
481  tctttaggtt taaaattaga tgcttgtcca ggtcgtttaa atcaaacttc aatgtttatt
541  aaagagaag gtgtatttta cggtcaatgt agtgaaatat gtggtataaa tcatggtttt
```

-continued

```
601 atgccaatag ttgttgaagc agtttcatta gaagattatt tagtttggtt aaaaaacaa
661 attaattttg attttaatgt ataa
``` c) Preparation and Application of Mixture to Treat Dermatophytoses and Tinea Unguium

TABLE 1

Composition of preparation for the treatment of dermatophytoses and tinea unguium

| Composition of dry mixture | Used component CAS No. | Weight % of component in dry substance | Weight % of component in aqueous suspension | Function of component |
|---|---|---|---|---|
| *Pythium oligandrum* (A) | — | 4 | 0.12 | Mycoparasitic component |
| Citric acid | 77-92-9 | 23 | 0.67 | Buffer |
| Sodium bicarbonate | 144-55-8 | 18 | 0.52 | Buffer/deodorant |
| Silicon oxide | 7631-86-9 | 8 | 0.23 | Adsorbent |
| PEG 6000 | 25322-68-3 | 3 | 0.09 | Moisturizer |
| Sodium carbonate | 497-19-8 | 2 | 0.06 | Buffer |
| Water content in aqueous application suspension (100 ml) | | | up to 100% | Application solvent |
| Concentration of viable cells of the mycoparasitic microorganism *Pythium oligandrum* | | | 50 viable cells per 1 ml of preparation in aqueous suspension | | d) Preparation and Application of Mixture to Eliminate Yeasts in Non-Healing Wounds

TABLE 2

Composition of preparation to eliminate yeasts in non-healing wounds

| Composition of dry mixture | Used component CAS No. | Weight % | % active substance in application | Function |
|---|---|---|---|---|
| *Pythium oligandrum* (B) | | 6 | 0.24 | Mycoparasitic component |
| Silicon oxide | 7631-86-9 | 94 | 3.76 | Adsorbent |
| Content of physiological solution in aqueous application suspension (250 ml) | | | up to 100% | |
| Concentration of viable cells of the mycoparasitic microorganism *Pythium oligandrum* | | | 30 viable cells per 1 ml of preparation in aqueous suspension | | e) Preparation and Application of Mixture to Eliminate Yeasts in the Oral Cavity

TABLE 3

Composition of preparation to eliminate yeasts in the oral cavity

| Composition of dry mixture | Used component CAS No. | Weight % of component in dry substance | Weight % of component in aqueous suspension | Function of component |
|---|---|---|---|---|
| *Pythium oligandrum* (C) | — | 4 | 0.16 | Mycoparasitic component |
| Citric acid | 77-92-9 | 31 | 0.90 | Buffer substance |
| Sodium bicarbonate | 144-55-8 | 27 | 0.79 | Buffer substance, deodorant |
| Sorbitol | 50-7-4 | 24 | 0.70 | Moisturizer |
| Silicon oxide | 7631-86-9 | 8 | 0.23 | Adsorbent |
| PEG 6000 | 25322-68-3 | 3 | 0.09 | Moisturizer |

TABLE 3-continued

Composition of preparation to eliminate yeasts in the oral cavity

| Composition of dry mixture | Used component CAS No. | Weight % of component in dry substance | Weight % of component in aqueous suspension | Function of component |
|---|---|---|---|---|
| Sodium carbonate | 497-19-8 | 2 | 0.06 | Buffer substance |
| D-Limonen | 5989-27-5 | 1 | 0.03 | Aroma |
| Water content in aqueous application suspension (100 ml) | | | up to 100% | |
| Concentration of viable cells of the mycoparasitic microorganism *Pythium oligandrum* | | | 10 viable oospores per 1 ml of preparation in aqueous suspension | |

Example 2

Suppression of Growth and Elimination of Dermatophytes and Yeasts in a Laboratory Test
(FIG. 1)

The application of the microorganism *Pythium oligandrum* in the form of encysted zoospores prepared according to the published protocol (5) was chosen for laboratory effectiveness tests. The suspension method of testing, which is preferred for the verification of the anti-microbial activities of other preparations (1), was chosen. Zoospores were encysted by vortexing for a period of 2 minutes, and maintained under these conditions at 16° C. until the beginning of the experiment. Suspensions of microconidia from the dermatophytes *Trichophyton interdigitale* var. *mentagrophytes* DMF2374, *Microsporum canis* CCM8353 and *Epidermophyton floccosum* PL231 and a suspension of *Candida albicans* CCM8261 yeasts were prepared according to the published methodologies (7, 1). The suspension of zoospores and the suspension of microconidia or yeast cells were diluted to the required concentration, and cells were cultivated in a suspension in six-well plastic dishes for a period of 48 hours at 30° C. Samples for determination of the number of living cells by the cultivation method were taken after 24 and 48 hours.

The result of the experiment is shown in FIG. 1. It is shown that in all tested cases, the quantity of encysted zoospores was optimum for suppressing the growth of the dermatophytes and pathogenic yeast *Candida albicans* being studied at between 10 and 50 viable cells per 1 ml of examined solution with dermatophyte or yeast. If the quantity of encysted zoospores was lower, the effective suppression of growth was not guaranteed. Surprisingly, not even a higher quantity of zoospores led to better results in suppressing the growth of the targeted microorganisms, this growth being either identical or higher.

Example 3

The Elimination of Dermatophytes and the Establishment of Physiological Microflora in Guinea Pigs Infected with Dermatophytes
(FIG. 2)

This test was conducted according to the published protocol (4, 7) with infection by verified strain of *Trichophyton interdigitale* var. *mentagrophytes* DMF2374. An identical mixture to that in the exemplary embodiment of this invention was used as a placebo during application, the cultivation biomass being replaced by water and a fungicidal substance according to exemplary embodiment 1c of this invention as the experimental substance.

The result of this test is described in in FIG. 2. The overall appearance of a treated guinea pig in the lower part of FIG. 2 and the histology of the skin of the animal and the value of the clinical dermatophytosis indexes of the animal clearly show the significant clinical effect in the treatment of experimental dermatophytosis in comparison with an animal treated using a placebo from which the active substance *Pythium oligandrum* was omitted.

Example 4

The Elimination of Dermatophytes and Improvement of the Clinical Condition of Patients with Tinea Unguium
(Table 4)

Table 4 on the next page shows the results of a study involving 21 patients affected by tinea unguium in combination with other dermatophytoses. Prior to the application of the preparation according to this invention, all 21 patients had positive findings by microscopy, and the occurrence of at least one dermatophyte, in some cases two dermatophytes, was confirmed in all the patients by cultivation. The occurrence of the pathogenic yeast *Candida albicans* was by far the most common among the accompanying microbiology. Most common in the accompanying diagnoses were diabetes, tinea pedis and tinea pedis *interdigitale*, and, in one case, a fungal disease of the hand was observed. One or more nails on the foot were affected to an average extent of 1.5 of the area of the nail.

The application of the preparation according to exemplary embodiment 1c was conducted for all patients in the study in the form of night nail wraps for two consecutive nights with application repeated after 14 days and one month.

An evaluation of effectiveness was conducted nine months after the end of application, which is 10 months after the beginning of the study. Most patients were negative under the microscope, while cultivation revealed that two patients had residual sporadic occurrence of the dermatophyte *Trichophyton rubrum*, this dermatophyte occurred to a heightened extent in one patient, and the *Candida albicans* yeast occurred sporadically in one patient. Overall, then, the level of mycological treatment could be evaluated as highly satisfactory, with the resolution of the mycological load in 95% of patients and clinical treatment evaluated on average at a level of 2.1 on the six-point scale (1—full treatment without malformation of nails, 6—deterioration in condition). In total, tinea unguium was cured in 12 patients without any malformation of the nails (54.5%), 1 patient was treated with residual malformation (4.5%), clinical improvement of more than 50% was evident in 6 patients (27.3%), there was insignificant improvement of up to 50% in one patient (4.5%) and there was no change in clinical condition in two patients even 9 months after the end of application (9.2%), although medical documentation would suggest a high likelihood of reinfection in these cases. There were no patients who suffered deterioration in clinical condition.

ment using commonly used medical preparations, including antibiotics, and for an even longer period for some patients (up to 2 years).

TABLE 4

Summary of clinical data for 21 patients suffering from tinea unguium

| No, Init, Age | Before application | | | | 3 months after application | | | | 9 months after application | | | | Final evaluation | | Participating |
| --- | --- | --- | --- | --- | --- | --- | --- | --- | --- | --- | --- | --- | --- | --- | --- |
| | Micr | Cult | Nail | Other | Micr | Cult | Nail | Other | Micr | Cult | Nail | Other | Mycol | Clin | dermatologist |
| 1, AV, 72 | y | Ab (m) | 0.4 | | n | | 0.2 | | n | | 0.1 | | 100 | 3 | Raj |
| 2, CJ, 77 | y | Tr (m), Ca (m) | 0.8 | | n | | 0.4 | | n | | 0 | | 100 | 2 | Bab |
| 3, CL, 45 | y | Tr (m), Ab (m) | 2.4 | | y | Tr (m) | 0.8 | | y | Tr (a) | 0.4 | | 63 | 3 | Vor |
| 4, GP, 55 | y | Ab (m) | 0.4 | dm | n | | 0.1 | dm | n | | 0 | dm | 100 | 1 | Vor |
| 5, HM, 71 | y | Tr (m) | 0.4 | dm | y | Tr (a) | 0.2 | dm | y | Tr (s) | 0.1 | dm | 50 | 3 | Kov |
| 6, IF, 40 | y | Ab (m), Ca (m) | 0.3 | ti | n | | 0.1 | | n | | 0 | | 100 | 1 | Vor |
| 7, IS, 52 | y | Tr (m), Ef (m) | 6 | hm | n | | 3 | | n | | 1 | | 100 | 3 | Bub |
| 8, IV, 76 | y | Tr (m), Ab (m) | 1.5 | | y | Tr (a) | 0.5 | | y | Tr (s) | 0.4 | | 88 | 3 | Raj |
| 9, KB, 55 | y | Tr (s), Ca (m) | 1 | | n | | 0.5 | | n | | 0 | | 100 | 1 | Nov |
| 10, KJ, 27 | y | Ab (a) | 0.3 | | n | | 0.1 | | n | | 0 | | 100 | 1 | Voj |
| 11, KK, 71 | y | Tr (m), Ef (a) | 2.5 | | n | | 2 | | n | | 1 | | 100 | 4 | Vor |
| 12, KS, 22 | y | Ab (a) | 0.5 | tp | n | | 0.1 | | n | | 0 | | 100 | 1 | Boh |
| 13, MK, 51 | y | Ab (a) | 3.1 | | n | | 2.4 | | n | | 3.2 | | 100 | 5 | Boh |
| 14, LM. 73 | y | Tr (m), Ca (m) | 1 | dm | n | | 0.4 | dm | n | | 0 | dm | 100 | 1 | Bub |
| 15, MH, 29 | y | Tr (m), Ca (m) | 0.6 | | n | | 0.2 | | y | Ca (s) | 0 | | 88 | 1 | Bub |
| 16, MP, 66 | y | Tr (m) | 1.5 | | n | | 0.8 | | n | | 0 | | 100 | 1 | Kov |
| 17, MS, 69 | y | Ab (m) | 1.3 | tp | n | | 0.6 | | n | | 0 | | 100 | 1 | Bub |
| 18, NB, 63 | y | Tr (m), Ab (m) | 3 | | n | | 1.8 | | n | | 0.8 | | 100 | 3 | Bub |
| 19, PM, 69 | y | Tr (m), Ca (m) | 1 | dm | n | | 0.8 | dm | n | | 0 | dm | 100 | 1 | Vor |
| 20, TM, 48 | y | Tr (m), Ab (a) | 2 | | n | | 0.8 | | n | | 0 | | 100 | 1 | Bub |
| 21, VJ, 70 | y | Ab (a) | 0.6 | ti | n | | 0.2 | | n | | 0 | | 100 | 1 | Bub |
| Average age | 58 | | 1.5 | | | | 0.81 | | | | 0.4 | | 95 | 2.1 | |
| S.D. | 17 | | 1.3 | | | | 0.83 | | | | 0.8 | | 17 | 1.4 | |

Abbreviations used:
No—number of patient in study,
Init—initials of patient,
Micr—microscopy in KOH,
Cult—cultivation result,
Nail - area of affected nail,
Other - other medical observations,
Mycol - evaluation of final mycological treatment,
Clin - final clinical evaluation of doctor on a six-point scale,
y - positive result,
n - negative result,
Ab—*Arthroderma benhamiae*,
Tr—*Trichophyton rubrum*,
Ca—*Candida albicans*,
Ef—*Epidermophyton floccosum*,
(m) - massive occurrence,
(a) - abundant occurrence,
(s) - sporadic occurrence,
dm—diabetes mellitus,
Ti—tinea interdigitale,
hm - mycosis of the hand,
tp—tinea pedis.

Example 5

The Suppression and Elimination of Pathogenic Yeasts in Non-Healing Wounds in Patients
(Table 5)

The influence of the application of the preparation according to this invention on a group of 12 patients with non-healing wounds complicated by yeast infection with the pathogenic yeasts *Candida albicans* was monitored in a preliminary practical study. Six of the patients suffered from diabetes, six did not. The average age of the patients in the diabetic group was 77.5 years and in the non-diabetic group 57.2 years. There is a predominance of women, who are known to have a higher susceptibility to the occurrence of varicose ulcers and non-healing wounds. It further ensues from the patients' anamnesis that there had been no advancement in the treatment of non-healing wounds for a minimum period of 6 months after the beginning of treatment using commonly used medical preparations, including antibiotics, and for an even longer period for some patients (up to 2 years).

Wet treatment was provided for patients with the use of a suspension prepared using preparations according to exemplary embodiment 1 d as part of wet healing. The application dressings were replaced every 8 hours for a total period of 4 days. The application described reduced the microbiological load very significantly, in that the occurrence of the pathogenic yeast was reduced by 95.3% in the case of diabetic patients and 75.3% in non-diabetic patients, a reduction of 85.3% being observed for the whole study. There was an improvement in the clinical picture of infection based on the evaluation of the participating doctors assessing the extent of the inflammatory process, the intensity of pus discharge etc. of 78.3% in diabetic patients and 67,2% in non-diabetic patients, meaning an improvement of 72.8% in total for the whole study. A highly significant correlation was found between the reduction of the microbial load and the improvement of the clinical picture of microbial infection, which is a very significant finding within the context of the published medical literature.

TABLE 5

Correlation of the improvement of the microbiological load and the improvement of clinical microbiology in 12 patients with non-healing wounds affected by yeast infection

| Initials, age, sex of patients | Improvement (%) in microbial status of patients | Improvement (%) in clinical status of patients | Correlation coefficient |
|---|---|---|---|
| Diabetic patients | | | |
| LS, 89, f | 72 | 60 | |
| LS, 87, f | 100 | 90 | |
| MM, 79, f | 100 | 90 | |
| ZM, 71, f | 100 | 90 | |
| MN, 70, m | 100 | 80 | |
| BR, 69, m | 100 | 60 | |
| Average age: 77.5 | 95.3 | 78.3 | 0.98 |
| Non-diabetic patients | | | |
| LK, 75, f | 32 | 28 | |
| BS, 66, f | 20 | 30 | |
| OK, 65, m | 100 | 90 | |
| OB, 54, f | 100 | 90 | |
| JJ, 44, f | 100 | 80 | |
| JS, 37, f | 100 | 85 | |
| Average age: 57.2 | 75.3 | 67.2 | 0.99 |
| Total for study: | 85.3 | 72.8 | 0.98 |

Example 6

The Suppression and Elimination of Pathogenic Yeasts in the Oral Cavity (Table 6)

A study was conducted among 12 patients with the presence of pathogenic yeasts in the oral cavity at dental hygiene ambulancies under the supervision of the stomatologists.

After microbiological sampling and clarification of the nature of the diagnosis, patients were informed and provided with one pack of the preparation to eliminate pathogenic yeasts in the oral cavity containing 5 effervescent tablets according to exemplary embodiment 1 d. After the evening oral hygiene, patients carefully washed the oral cavity and followed this by rinsing with the preparation for at least five minutes on the condition that it contained an average of 10 viable oospores of the microorganism Pythium oligandrum after prior activation in lukewarm water. The oral cavity was not rinsed after this so that the remainder of the application solution would remain there overnight. The application was repeated in the morning and patients continued in this way for a period of 5 days, using the 5 effervescent tablets in the pack.

Subsequent clinical monitoring and evaluation of effectiveness then proceeded around 6 months after application. The pathogenic yeast was eliminated from the oral cavity in 67.1% of cases, this accompanied by an average improvement in the clinical condition of the affected patients by 66.8%. Patients mainly suffered from repeat inflammations of the oral cavity and periodontal diseases. A correlation was again identified between the reduction in the occurrence of yeasts in the oral cavity and an improvement in clinical condition.

TABLE 6

Correlation of the improvement of the microbiological load and an improvement in the clinical condition of 10 patients with yeast infection in the oral cavity

| Initials, age, sex of patients | Improvement (%) in microbial status of patients | Improvement (%) in clinical status of patients | Correlation coefficient |
|---|---|---|---|
| CJ, 40 | 75 | 50 | |
| HL, 38 | 75 | 66 | |
| JJ, 39 | 75 | 67 | |
| KA, 26 | 50 | 40 | |
| LI, 60 | 80 | 76 | |
| PP, 74 | 50 | 70 | |
| SK, 35 | 70 | 66 | |
| SM, 37 | 75 | 82 | |
| SS, 34 | 50 | 54 | |
| ZK, 35 | 75 | 80 | |
| Average | 67.1 | 66.8 | 0.95 |

INDUSTRIAL APPLICABILITY

The preparation for the treatment of dermatophytoses and yeast infections on the skin and mucous membranes could be used to suppress symptoms associated with infection by dermatophytes or yeasts on the skin and mucous membranes, such as socially troublesome smell symptoms, excessive perspiration of the foot, irritation and burning, and for the suppression and elimination of the occurrence of dermatophytes and yeasts in non-healing wounds, in the oral cavity, on the skin, on the urogenital mucous membranes, in the hair and in other places affected by these microorganisms.

CITED LITERATURE

1. Barros M E S, Santos D A, Hamdan J S (2006) *Mycol Res* 110, 1355-1360.
2. Calderona R A, Fonzi W A (2001) *Trends Microbiol* 9, 327-335.
3. Horner N R, Grenville-Briggs U, van West P (2012) *Fungal Biol* 116, 24-41.
4. Klimeš R, Suchánek M, Maštalková L et al (2016) *Vet Dermatol*, in print.
5. Madsen A M, Robinson H L, Deacon J W (1995) *Mycol Res* 99, 1417-1424.
6. Martinez D A, Oliver B G, Graser Y et al (2012) *mBio* 3, e00259-12.
7. Saunte D M, Simmel F, Frimodt-Moller N (2007) *Antimicrob Agents Chemother* 51, 3317-3321.
8. CZ 302297 (published 2011) Suchánek M, Klimeš R
9. CZ 28816 U (published 16 Nov. 2015) Suchánek M, Klimeš R
10. CZ 9883 U (published 14 Apr. 2000) Veselý D, Veselý L
11. Yacoub A, Berger H, Gerbore J et al. (2016) *Genome Announcements* 4, e00215-16.

The invention claimed is:

1. A preparation containing the mycoparasitic microorganism *Pythium oligandrum* for the treatment of dermatophytoses and yeast infections on the skin and mucous membranes obtained from a dry mixture containing 0.1 to 99.9% weight mycoparasitic microorganism *Pythium oligandrum* and 0.1 to 99.9% auxiliary substances, containing at least one component from a group comprising adsorbent, buffer, moisturizer, deodorant and aroma, wherein the preparation contains 1 to 500 viable cells of the microorganism

*Pythium oligandrum* per 1 ml of applied preparation in an aqueous suspension at the site of application, and wherein the viable cells of the microorganism *Pythium oligandrum* comprise dormant oospores, encysted zoospores, and viable coenocytic mycelium.

2. The preparation according to claim 1 wherein the preparation contains 10 to 50 viable cells of the microorganism *Pythium oligandrum* per 1 ml of applied preparation in an aqueous suspension.

3. A method of applying the preparation of claim 1 containing the mycoparasitic microorganism *Pythium oligandrum* for the treatment of dermatophytoses and yeast infections on to the affected areas of the skin and mucous membranes.

4. The method of applying the preparation according to claim 3 characterized in that for the treatment of dermatophytoses in the form of tinea unguium the preparation containing 50 viable cells per 1 ml of preparation in an aqueous suspension is applied to the affected areas in the form of a wet suspension.

5. The method of applying the preparation according to claim 3 characterized in that for the treatment of dermatophytoses in the form of tinea unguium the preparation containing 50 viable cells per 1 ml of preparation in an aqueous suspension is applied to the affected areas in the form of creams, gels, ointments, wet wipes, antimicrobial sprays, moisturized patches and moisturized powders.

6. The method of applying the preparation according to claim 3 for the treatment of yeast infections in non-healing wounds characterized in that for the treatment of yeast infections in non-healing wounds the preparation is applied in the form of wet compresses containing 30 viable cells per 1 ml of preparation in an aqueous suspension in a physiological solution, and subsequent replacement of wet compresses containing 30 viable cells per 1 ml of preparation in an aqueous suspension after 8 hours for a period of 4 days.

7. The method of applying the preparation according to claim 3 characterized in that the preparation is applied using wet healing products in the form of creams, ointments, wet wipes, antimicrobial sprays, moisturized patches and powders containing 30 viable cells per 1 ml of preparation in an aqueous suspension and subsequently replacing these wet-healing products every 8 hours for a period of 4 days.

8. The method of applying the preparation according to claim 3 for the treatment of yeast infections in the oral cavity characterized in that the application is made by rinsing with the preparation containing 10 viable cells per 1 ml of preparation in an aqueous suspension, in that the rinses are done at least twice a day for a period of 5 consecutive days.

9. The method of applying the preparation according to claim 3 characterized in that the application is made using a preparation containing 10 viable cells per 1 ml of preparation in an aqueous suspension that is part of toothpastes, gels or oral sprays or the application is made by introducing an aqueous suspension to the oral cavity using syringe and needle, in that such applications are made at least twice a day for a period of 5 consecutive days.

10. A method of applying the preparation of claim 2 containing the mycoparasitic microorganism *Pythium oligandrum* for the treatment of dermatophytoses and yeast infections on to the affected areas of the skin and mucous membranes.

11. The method of applying the preparation according to claim 10 characterized in that for the treatment of dermatophytoses in the form of tinea unguium the preparation containing 50 viable cells per 1 ml of preparation in an aqueous suspension is applied to the affected areas in the form of a wet suspension.

12. The method of applying the preparation according to claim 10 characterized in that for the treatment of dermatophytoses in the form of tinea unguium the preparation containing 50 viable cells per 1 ml of preparation in an aqueous suspension is applied to the affected areas in the form of creams, gels, ointments, wet wipes, antimicrobial sprays, moisturized patches and moisturized powders.

13. The method of applying the preparation according to claim 10 for the treatment of yeast infections in non-healing wounds characterized in that for the treatment of yeast infections in non-healing wounds the preparation is applied in the form of wet compresses containing 30 viable cells per 1 ml of preparation in an aqueous suspension in a physiological solution, and subsequent replacement of wet compresses containing 30 viable cells per 1 ml of preparation in an aqueous suspension after 8 hours for a period of 4 days.

14. The method of applying the preparation according to claim 10 characterized in that the preparation is applied using wet healing products in the form of creams, ointments, wet wipes, antimicrobial sprays, moisturized patches and powders containing 30 viable cells per 1 ml of preparation in an aqueous suspension and subsequently replacing these wet-healing products every 8 hours for a period of 4 days.

15. The method of applying the preparation according to claim 10 for the treatment of yeast infections in the oral cavity characterized in that the application is made by rinsing with the preparation containing 10 viable cells per 1 ml of preparation in an aqueous suspension, in that the rinses are done at least twice a day for a period of 5 consecutive days.

16. The method of applying the preparation according to claim 10 characterized in that the application is made using a preparation containing 10 viable cells per 1 ml of preparation in an aqueous suspension that is part of toothpastes, gels or oral sprays or the application is made by introducing an aqueous suspension to the oral cavity using syringe and needle, in that such applications are made at least twice a day for a period of 5 consecutive days.

* * * * *

SEQUENCE LISTING

<160> NUMBER OF SEQ ID NOS: 2

<210> SEQ ID NO 1
<211> LENGTH: 759
<212> TYPE: DNA
<213> ORGANISM: Pythium oligandrum, strain M1
<220> FEATURE:
<221> NAME/KEY: ITS rRNA gene

<400> SEQUENCE: 1

```
atcattacca caactaaaaa ctttccacgt gaaccgttat aactatgttc tgtgcttcgt      60
cgcaagactt gaggctgaac gaaggtgagt ctgcgtctat tttggatgcg gatttgctga     120
tgttatttta aacacctatt acttaatact gaactatact ccgaatacga aagtttttgg     180
ttttaacaat taacaacttt cagcagtgga tgtctaggct cgcacatcga tgaagaacgc     240
tgcgaactgc gatacgtaat gcgaattgca gaattcagtg agtcatcgaa attttgaacg     300
catattgcac tttcgggtta tgcctggaag tatgcctgta tcagtgtccg tacatcaaac     360
ttgcctttct ttttttgtgt agtcaaaatt agagatggca gaatgtgagg tgtctcgcgc     420 tgtctttta aagatggttc gagtcccttt aaatgtacgt tgattctttc ttgtgtctgc     480
gaattgcgat gctatgctct ttgtgatcgg tttagattgc tttgcgctgg tgggcgactt     540
cggttaggac atatggaagc aacctcaatt ggcggtatgt tcggctttgc ctgacgttaa     600
gctaagcgag tgtagttttc tgtcttttcc ttgaggtgta cctgtcgtgt gtgaggttga     660
tttaggctat atggttgctt ggttgtgtgg tttagcgttt tcagacgcct gcttcggtag     720
gtaaaggaga caacaccaat ttgggactga gagtttact                            759
```

<210> SEQ ID NO 2
<211> LENGTH: 683
<212> TYPE: DNA
<213> ORGANISM: Pythium oligandrum, strain M1
<220> FEATURE:
<221> NAME/KEY: Mitochondrial COXII cytochrome oxidase

<400> SEQUENCE: 2

```
atggaaggta ttattaactt tcatcatgat ttagtatttt ttttaattat tgtgactgtt      60
tttgtttgtt ggttattatt tagagtaatc gtattattcg atgaaaaaaa aaacccaata    120
cctgctacat ttgtacatgg agcaactatt gaaattattt ggacaacaat tccagcatta    180
attttattaa ccgtagcagt tccatctttt gctttattat attcaatgga tgaaattatt    240
gatccaatta taactttaaa agtaataggt agtcaatggt actggagtta tgaatattct    300
gataatttag aatttgcaga tgaaccttta atttttgata gttacatggt tcaagataat    360
gacttagaaa taggacaatt taggttatta gaagtagaca accgtgttgt tgtaccaact    420
aatagccata ttagagtttt aataacagct tctgacgttt tacattcatg gctataccc    480 tctttaggtt taaaattaga tgcttgtcca ggtcgtttaa atcaaacttc aatgtttatt    540
aaaagagaag gtgtatttta cggtcaatgt agtgaaatat gtggtataaa tcatggtttt    600
atgccaatag ttgttgaagc agtttcatta gaagattatt tagtttggtt aaaaaacaaa    660
ttaattttga ttttaatgta taa                                             683
```